United States Patent
Wang et al.

(10) Patent No.: US 8,309,490 B2
(45) Date of Patent: Nov. 13, 2012

(54) LOW VOC AND STABLE PLANT GROWTH REGULATOR LIQUID AND GRANULE COMPOSITIONS

(75) Inventors: Yueh Wang, Arlington Heights, IL (US); John Lopez, Gurnee, IL (US); Ayyappan Nair, Des Plaines, IL (US); Zhengyu Huang, Buffalo Grove, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 28 days.

(21) Appl. No.: 12/890,048

(22) Filed: Sep. 24, 2010

(65) Prior Publication Data

US 2011/0071030 A1     Mar. 24, 2011

Related U.S. Application Data

(60) Provisional application No. 61/245,337, filed on Sep. 24, 2009.

(51) Int. Cl.
*A01N 25/00*     (2006.01)
*A01N 65/00*     (2009.01)
*A01N 43/40*     (2006.01)

(52) U.S. Cl. ............ 504/116.1; 504/189; 504/244
(58) Field of Classification Search ............ 504/116.1
See application file for complete search history.

(56) References Cited

U.S. PATENT DOCUMENTS

| 7,906,459 B2* | 3/2011 | Wang et al. ............ 504/130 |
| 2008/0300313 A1* | 12/2008 | Byrne et al. ............ 514/611 |

OTHER PUBLICATIONS

U.S. Appl. No. 12/713,332, filed Feb. 2010, Wang et al.*

* cited by examiner

*Primary Examiner* — Mina Haghighatian
*Assistant Examiner* — Mei-Ping Chui
(74) *Attorney, Agent, or Firm* — Wood, Phillips, Katz, Clark & Mortimer

(57) ABSTRACT

The invention relates to low VOC plant growth regulator compositions comprising less than about 25% of volatile organic compounds (VOCs). The compositions comprise forchlorfenuron (CPPU). Also provided are methods of using the compositions.

6 Claims, No Drawings

LOW VOC AND STABLE PLANT GROWTH REGULATOR LIQUID AND GRANULE COMPOSITIONS

FIELD OF THE INVENTION

The present invention relates to stable and water-soluble plant growth regulator compositions with low amounts of volatile organic compounds (VOCs).

BACKGROUND OF THE INVENTION

The present invention generally relates to stable and water-soluble plant growth regulator compositions with low amounts of volatile organic compounds (VOCs).

Plant growth regulators are useful for influencing a range of plant developmental processes including stem elongation, germination, dormancy, flowering, sex expression, enzyme induction, fruit size and quality, as well as leaf and fruit senescence. Plant growth regulators may be formulated in at least five different types of formulations: 1) solutions, 2) wettable powders, 3) soluble powders, 4) tablets and 5) water-soluble or dispersible granules.

Cytokinins are a class of plant growth regulators which are generally defined as N6-substituted adenine derivatives such as trans-zeatin, 6-benzyladenine (6-BA) and kinetin. Recently, a new class of cytokinins has been identified which possess N-phenylurea substituted structure such as forchlorfenuron (CPPU) and thidiazuron (TDZ). Cytokinins are of extreme importance in regulating plant growth and development, especially cell division. They are marketed under various trade names and are commercially used in fruit thinning and sizing as well as pre- and post-harvest treatments of ornamental plants and flowers.

6-BA and CPPU have very low water solubility of 44 and 39 ppm at 25° C., respectively. Alcoholic solvents such as IPA, THFA and propylene glycol are being employed in conventional liquid plant growth formulations. For example, US Patent Application US 2008/0039322 A1 discloses cytokinin solution formulations comprising propylene glycol. However, one of the disadvantages of alcoholic solvents is that they are considered volatile organic compounds (VOCs) having relatively high photochemical reactivity for ground level ozone formation and, therefore, may be harmful to the environment. The United States Environmental Protection Agency (EPA) estimates the maximum incremental reactivity (MIR) of volatile organic compounds or solvents which can participate in atmospheric photochemical reactions (MIR measures grams ozone produced per grams VOC).

Various regulatory agencies, such as the EPA, the California Department of Pesticide Regulation (DPR) and Air Resources Board (CARB) seek to lower the VOC content in various agricultural products and fumigants.

There is a significant formulation challenge to meet the requirements of lowering the VOC content while preserving product stability and effectiveness.

There is, therefore, a need to develop effective plant growth regulator compositions that contain low amounts of VOCs.

BRIEF SUMMARY OF THE INVENTION

The present invention is generally directed to stable, water-soluble, low VOC plant growth regulator compositions. The compositions of the present invention comprise less than about 25.0% by weight of volatile organic compounds (VOCs) measured by Thermogravimetric Analysis (TGA).

In another embodiment, an aqueous composition of the present invention comprises from about 0.1% to about 5.0% by weight of forchlorfenuron, an acid, a surfactant and water, wherein the weight percentages are based on the total weight of the plant growth regulator composition.

In yet another embodiment, an aqueous composition of the present invention comprises from about 0.5% to about 1.5% by weight of forchlorfenuron, an acid, a surfactant and water, wherein the weight percentages are based on the total weight of the plant growth regulator composition.

In a preferred embodiment, the acid is lactic acid.

In another preferred embodiment, the surfactant is selected from the group consisting of ethoxylated alkyl alcohols, sodium dioctyl sulfosuccinates, ethoxylated fatty acids, ethoxylated vegetable oils, glycol esters, sorbitan fatty acid esters, ethoxylated sorbitan fatty acid esters, ethylene oxide/propylene oxide block copolymer and combinations thereof. Most preferably, the surfactant is an ethoxylated alkyl alcohol.

In a preferred embodiment, a low VOC composition of the present invention comprises from about 0.5% to about 1.5% by weight forchlorfenuron; from about 15.0 to about 30.0% by weight lactic acid (80%); from about 5.0% to about 15% by weight of an ethoxylated alkyl alcohol; and from about 50% to about 80% by weight distilled water.

In another preferred embodiment, a low VOC composition of the present invention comprises about 1.0% by weight of forchlorfenuron; about 20.0% by weight of lactic acid; about 10.0% by weight of an ethoxylated alkyl alcohol; and about 69.0% by weight of water, wherein the weight percentages are based on the total weight of the plant growth regulator composition.

Additionally, the compositions of the present invention may further comprise an antioxidant. The antioxidant may be propyl gallate, ethoxyquin, butylated hydroxyanisole, butylated hydroxytoluene, tertiary butylhydroquinone and combinations thereof. The preferred antioxidant is propyl gallate.

The compositions may also contain at least one additional component such as a sticker, a spreader sticker, a systemic acquired resistance inducer, an anti-foaming agent, a preservative, a humectant, a dye, a U.V. protectant, a buffer, a carrier or a combination thereof.

In another embodiment, the invention relates to a ready-to-use product prepared from the compositions of the present invention. The ready-to-use products may be spray-applied to plants in order to improve plant growth, yield, fruit thinning, fruit sizing, flowering and quality.

The invention is also directed to a method of regulating plant growth comprising the step of treating soil, a seed or a plant with an effective growth-regulating amount of the compositions described above.

These and other features, aspects, advantages of the present invention will become better understood with reference to the following description and appended claims.

DETAILED DESCRIPTION OF THE INVENTION

The present invention generally relates to stable, water-soluble and low VOC plant growth regulator compositions. All compositions of the present invention comprise less than about 25.0% by weight of volatile organic compounds (VOCs).

We have surprisingly discovered that water-insoluble forchlorfenuron can be dissolved in lactic acid in conjunction with a surfactant. Therefore, soluble aqueous formulations of forchlorfenuron that comprise less than about 25.0% by weight of VOCs can be prepared.

The phrase "plant growth regulator" as used herein connotes a product which serves to modify the growth and the development of a treated plant to agricultural maturity without killing the plant. Such modification may result from the effect of the material on the physiological processes of the plant, or from the effect of said material on the morphology of the plant. These modifications may also result from any combination or sequence of physiological or morphological factors.

In one embodiment, a composition of the present invention comprises from about 0.1% to about 5.0% by weight of forchlorfenuron, an acid, a surfactant and water, wherein the weight percentages are based on the total weight of the plant growth regulator composition.

In yet another embodiment, a composition of the present invention comprises from about 0.5% to about 1.5% by weight of forchlorfenuron, an acid, A surfactant and water, wherein the weight percentages are based on the total weight of the plant growth regulator composition.

The preferred acid is lactic acid.

In the compositions of the present invention, a non-ionic surfactant is used as a wetting, solubilizing, binding and penetrating agent. Non-ionic surfactants include ethoxylated alkyl alcohols such as TOMADOLS®, ethoxylated vegetable oils such as AGNIQUE SBO® (soybean), CSO (castor) and RSO (rapeseed), ethoxylated sorbitan esters such as EMSORB®, TWEEN®, and T-MAZE®; sorbitan fatty acid esters such as SPAN® and ALKAMUL®, sucrose and glucose esters and derivatives thereof such as MAZON®, RHEOZAN® and GLUCOPON®; ethoxylated alcohols such as TRYCOL®, BRIJ®, ARMIX®, TERGITOL® and PLURAFAC®; ethoxylated alkylphenols such as IGEPAL®, MACOL® and TRITON®; ethoxylated fatty amines such as TRYMEEN® and ETHOMEEN®; ethoxylated fatty acids such as EMEREST®, ALKAMUL® and TRYDET®; ethoxylated fatty esters such as ALKAMUL® and ATLAS G®; fatty acids such as ATLAS G-1556®; glycerol esters such as MAZOL GMO®; glycol esters such as GLYCOL SEG®; lanolin-based derivatives such as AMERCHOL CAB®; methyl esters such as OLEOCAL ME®; monoglycerides and derivatives such as ETHOSPERSE G-260; propoxylated and ethoxylated fatty acids such as ANTAROX AA-60®; block copolymers of ethylene oxide and propylene oxide such as PLURONIC® or SURFONIC®; silicone-based surfactants such as SILWET®, BREAKTHRU® and mixtures of organosilicon surfactants with non-ionic or ionic surfactants; polysaccharides, copolymers of acrylamide and acrylic acid; and acetylenic diol derivatives such as SURFYNOL 104® or tristyrylphenols such as SOPROPHOR® among others.

A presently preferred nonionic surfactant family is the ethoxylated alkyl alcohols of C9 to C15 chains (TOMADOL 25-7, 1-7 or 91-6®).

The surfactants' tradenames are often common to a class or series of surfactants. Therefore, where a tradename is mentioned, any surfactant in the family including that tradename will be suitable.

Other components of the compositions may include additional surface active agents, dyes, stickers, spreader stickers, U.V. (ultra-violet) protectants, systemic acquired resistance inducers, preservatives, humectants, antioxidants, antifoams, buffers, carriers, or other components or combinations thereof which facilitate product handling and application. The antioxidant may be propyl gallate, ethoxyquin, butylated hydroxyanisole, butylated hydroxytoluene, tertiary butylhydroquinone and combinations thereof.

In a preferred embodiment, a low VOC composition of the present invention comprises from about 0.5% to about 1.5% by weight forchlorfenuron; from about 15.0% to about 30.0% by weight lactic acid (80%); from about 5.0% to about 15% by weight of an ethoxylated alkyl alcohol; and from about 50% to about 80% by weight distilled water.

In yet another preferred embodiment, a low VOC composition of the present invention comprises about 1.0% by weight of forchlorfenuron, about 20.0% by weight of lactic acid, about 10.0% by weight of the ethoxylated alkyl alcohol and about 69.0% by weight of water, wherein the weight percentages are based on the total weight of the plant growth regulator composition.

In another embodiment, the invention relates to a ready-to-use product prepared from the compositions of the present invention. It is well within a skill of the art to prepare such ready-to-use products using well-known techniques, such as dilutions. The dilutions may be made in water and spray-applied in order to improve plant growth, yield, fruit thinning, fruit sizing, flowering and quality. In one embodiment, the compositions of the present invention are themselves ready-to-use products. It is also contemplated that the ready-to-use compositions of this invention may be used in other active ingredients, such as herbicides, fungicides, insecticides, nematicides, biochemical pesticides, plant produced pesticides (botanicals) or plant nutrients.

The compositions described above may be used to regulate plant growth of fruit-producing plants, vegetable-producing plants, row crops, vegetable crops, grasses or trees. The benefits of using the compositions of the present invention vary according to the type of plant treated. For example, in grapes, treatment with the compositions can lead to cluster elongation, thinning and larger grapes. In oranges, lemons, limes and tangerines, the formulation can lead to a delay in the aging of the rind and reduce disorders such as rind staining, water spotting, sticky or tacky surface, puffy rind or rupture under pressure. In cherries, the compositions may advantageously be used to produce larger, brighter colored and/or firmer fruit.

The compositions of the present invention are preferably diluted in water and sprayed on the plant or tree to be treated. The spraying may be by conventional ground or aerial application equipment. Spray volumes are variable depending upon the orchard or crop, growth stage and climatic conditions. The range may be 5 gallons to 300 gallons/acre or higher. A presently preferred range is between 100 to 250 gallons per acre by pressurized spray application equipment. To prepare a composition for application, a tank is half-filled with water, followed by spray addition of adjuvant, and then addition of the plant growth regulator composition, followed by addition of more water and mixing for at least 15 minutes prior to actual spraying.

Alternatively, the compositions of the present invention may be directly applied to the soil (in which the plant will be grown or is growing) with or without granular fertilizers for the improved growth and maintenance of crops.

Moreover, the compositions of the present invention may be applied to seeds to achieve the same effect. The seed may be rice or paddy, alfalfa, cotton, sorghum, soybeans, corn or other vegetables, ornamental or turf and pasture grass seed, among others.

The concentration of the plant growth regulator will vary depending upon the type of fruit is to be treated, the peculiarities of the locale, and the desired result. In general, the composition may be applied at a field rate of from about 0.01 to about 1.0 lb per acre; preferably at a rate of from about 0.02 to about 0.5 lbs per acre and most preferably at a rate of from about 0.02 to about 0.2 lbs/acre. For example, the field spray rates for grapes using CPPU can be about 4-8 g/250 gallons per acre.

A single application may be enough, though depending upon the particular fruit and desired results, multiple applications may be made.

As used herein the term "plant" includes fruit-producing plants, vegetable-producing plants, row crops, vegetable crops, grasses and trees.

The fruit may be grapes, cherries, lemons, limes, oranges, grapefruit, strawberries, pineapples, stone fruits, apples, pears, peaches, blueberries, pistachio or tangerines, among others. The row crop may be cotton, soybeans, corn, sugar cane or rice, among others. The vegetable crops may be lettuce, artichokes, celery or peppers among others. The grasses may be Bahaigrass (*Paspalum notatum* Flugge), Bentgrass (*Agrostis* L.), Bermudagrass (*Cynodon dactyion* L.), Carpetgrass (*Axonopus affinis* Chase), Kentucky bluegrass (*Poa pratensis* L.). Canada Blugrass (*Poa compressa* L.), Buffalograss (*Buchloe dactyloides* (Nutt.) Englem.), Fescue grasses (*Festuca*), annual Rye grass (*Lolium L. multiflorum* Lam.), perennial Rye grass (*Lolium perenne* L.), Saint augustinegrass (*Stenotaphrum secundatum* Kuntze), Japanese lawngrass (*Zoysia japinica* Steud.), Centipedegrass (*Eremochloa ophiuroides* (Munro) Hacck, other turf grasses for residential or commercial establishments, among others.

As used herein, all numerical values relating to amounts, weight percentages and the like, are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

The invention will be understood more clearly from the following non-limiting representative examples. Of course, the present invention is not limited to the particular embodiments and modes of operation described herein and it is possible to imagine a number of variations in the details without departing from the scope of this invention.

The example below is presented to describe preferred embodiments and utilities of the invention and is not meant to limit the invention unless otherwise stated in the claims appended hereto.

EXAMPLE

Example

Low VOC 1% CPPU Aqueous Composition

TABLE 1a

Low VOC CPPU Aqueous Compositions

| Components | Wt % |
|---|---|
| Forchlorfenuron (98%) | 1.0 |
| Lactic Acid (80%) | 25.0 |
| Tomadol ® 25-7 | 10.0 |
| Distilled Water | 64.0 |

Table 1a shows the percent weight of the components of low VOC plant growth composition. The composition is a 1% CPPU Microemulsion Concentrate (MEC) composition with 10% Tomadol surfactant. High surfactant level is needed to prevent the crystallization of CPPU in cold storage and use dilution. The pH of the composition was measured at 1.72.

The composition has low VOC content which was demonstrated by TGA. According to TGA, VOC content of the composition was about 19.05%.

The compositions were prepared by dissolving the forchlorfenuron in the lactic acid with mixing, and then diluting with water and surfactant.

The compositions were sprayed on greenhouse tomato plants and did not exhibit phytotoxicity.

TABLE 1b

Storage Stability of Low VOC CPPU MEC Composition (HPLC Assay)

| Temperature and Time | |
|---|---|
| Initial Value | 1.05 |
| 54° C./2 weeks | 1.03 (99%) |
| 25° C./6 months | 1.01 (96%) |
| 25° C./12 months | 1.01(96%) |
| Ambient room temperature (approx. 20-22 C.)/47 months | 1.01 (96%) |

Table 1b shows that the low VOC composition of Table 1a exhibits good storage stability after up to 47 months at ambient room temperature, 12 months of storage at 25° C. and 2 weeks at 54° C.

We claim:

1. A low VOC plant growth regulator composition consisting of:
 a. from about 0.1% to about 5.0% by weight of forchlorfenuron;
 b. from about 15.0% to about 30% by weight of lactic acid;
 c. from about 5.0% to about 15% by weight of an ethoxylated alkly alcohol; and
 d. water,
 wherein the weight percentages are based on the total weight of the plant growth regulator composition.

2. The composition of claim 1, wherein the amount of forchlorfenfuron is from about 0.5% to about 1.5% by weight.

3. The composition of claim 1, wherein the amount of forchlorfenuron is from about 0.5% to about 1.5% by weight and the amount of water is from about 50% to about 80% by weight.

4. The composition of claim 1, wherein the amount of forchlorfenuron is about 1.0% by weight, the amount of lactic acid is about 20.0% by weight, the amount of the ethoxylated alkyl alcohol is about 10.0% by weight, and the amount of water is about 64.0% by weight.

5. A ready-to-use product prepared from the composition of claim 1.

6. A method of treating plants comprising applying an effective amount of the composition of claim 1 to said plants.

* * * * *